United States Patent [19]

Perlman et al.

[11] Patent Number: 4,526,752
[45] Date of Patent: Jul. 2, 1985

[54] OXYGEN INDICATOR FOR PACKAGING

[76] Inventors: Daniel Perlman, 94 Oakland Ave., Arlington, Mass. 02174; Henry Linschitz, 35 Riverside Dr., Waltham, Mass. 02154

[21] Appl. No.: 450,234

[22] Filed: Dec. 16, 1982

[51] Int. Cl.³ .............................. G01N 21/78
[52] U.S. Cl. ........................ 422/56; 116/207; 206/459; 206/807; 422/58; 422/87; 427/7; 436/1; 436/136; 436/904
[58] Field of Search ............... 436/1, 136, 138, 904; 422/56, 57, 58, 83, 86, 87; 116/207; 206/807, 569, 459

[56] References Cited

U.S. PATENT DOCUMENTS

| | | |
|---|---|---|
| 1,055,595 | 3/1913 | Atkins . |
| 1,095,313 | 5/1914 | Davids . |
| 1,910,952 | 5/1933 | Hensmanns . |
| 2,063,245 | 12/1936 | Haessler . |
| 2,967,092 | 1/1961 | Buchoff et al. . |
| 3,067,015 | 12/1962 | Lawdermilt . |
| 3,451,741 | 6/1969 | Manos . |
| 3,463,532 | 8/1969 | Chidley et al. . |
| 3,505,020 | 4/1970 | Caldwell . |
| 3,672,842 | 6/1972 | Florin . |
| 3,681,027 | 8/1972 | Smith . |
| 3,800,780 | 4/1974 | Elliott ........................ 436/1 X |
| 3,899,295 | 8/1975 | Halpern . |
| 3,963,442 | 6/1976 | Bullard et al. ............ 422/55 X |
| 4,098,577 | 7/1978 | Halpern . |
| 4,169,811 | 10/1979 | Yoshikawa et al. . |
| 4,349,509 | 9/1982 | Yoshikawa et al. . |

Primary Examiner—Arnold Turk
Attorney, Agent, or Firm—Weingarten, Schurgin, Gagnebin & Hayes

[57] ABSTRACT

A tamper-resistant package containing in an anerobic environment a leuco dye free of reducing agent which dye becomes colored upon reaction with oxygen.

21 Claims, 3 Drawing Figures

OXYGEN INDICATOR FOR PACKAGING

BACKGROUND OF THE INVENTION

This invention relates to an indicator in a package which will show whether or not the original seal on the package has been broken and contents exposed to air. In particular it relates to packages of food, pharmaceuticals, chemical materials, clinicals and similar materials to detect and demonstrate whether there has been any tampering. Various methods for ascertaining the integrity of a package have been previously described using certain chemical and physical tests to indicate a change in the environment within the package. Thus, a change in moisture content, exposure to light, loss of packaging gas and color changes resulting from the presence of oxygen have all been suggested. Representative prior art includes U.S. Pat. Nos. 1,910,952; 1,055,595; 1,095,313; 3,899,295; 4,098,577; 3,463,532; 4,169,811; and 4,349,509.

However, the prior art devices and methods suffer from one or more disadvantages as, for example, high cost, lack of reliability, and insufficient protection against deliberate tampering.

One object of the present invention is to provide within a sealed package an indicator which will show in a reliable way whether or not the package has been opened.

A further object of this invention is to provide such an indicator having greater resistance to tampering than prior art devices and methods.

Other objects and advantages of this invention will be apparent from the description and claims which follow, taken together with the appended drawing.

SUMMARY OF THE INVENTION

The invention comprises, in general, the utilization of a substrate carrying, in leuco form, a dye free of reducing agent as an indicator. The dye is characterized by the reactivity of its leuco form with oxygen to change from the leuco to the colored state, and being reactive with reducing agent, to change from the colored state to the leuco state. Examples of such dyes are basic thiazine dyes such as methylene blue and new methylene blue. Other examples are triphenylmethane dyes such as methyl violet.

The indicator is applied to the substrate in an atmosphere free of oxygen. Thus, methylene blue is dissolved in water to which is added a volatile reducing agent such as a mixture of ammonium hydroxide and acetaldhyde. By "reducing agent" is meant any combination of reductant and auxiliary reagents that catalyze rate of reduction. These auxiliary reagents may be volatile as well. The volatile reducing agent is removed in any environment free of air as, for example, vacuum or nitrogen, carbon dioxide or argon gas leaving only the reduced dye (leuco) on the substrate. The package is sealed so as to maintain the anerobic environment within the package. In this manner, the deposited dye, which can be positioned to show the integrity of the package through a transparent cap, will immediately transform to the colored state if there is any oxygen admitted, as would take place by opening of the package. The color could be shown in a predetermined pattern, either in words or symbols. Thus, the word "OPENED" printed in invisible reduced dye would become colored upon exposure to air. In contrast to prior art methods and devices, it would be very difficult in the absence of available reducing agent to reduce the colored warning to its previous invisible state. Further, any attempt to so reduce the color by external means would cause distortion or smudging of the colored warning.

Thus, the elimination of the reducing agent has rendered the indicator far more tamper-resistant than the prior art. The dye cannot spontaneously revert to its reduced form if oxygen is displaced from the container. Also, the dye will be more stable upon long-term storage in the absence of oxygen and thus have an improved shelf life.

The dyes that are suitable for use in this invention can be deposited on almost any inert surface such as paper or plastic. Volatile materials other than ammonium hydroxide which can be used in this invention include triethyl amine and mixtures thereof with ammonium hydroxide. Other volatile reducing agents include 2-mercaptoethanol, ethanethiol, and formaldehyde.

Unlike the prior art which suggests that a solvent is needed to obtain a sensitive oxygen indicator, the indicator of this invention, which is pure reduced dyestuff, is quite sensitive to the presence of oxygen when it is dry. Although it is preferable in this invention to remove the reducing agent by having it volatilized, it is also possible, through less desirable, to wash reduced dyes with oxygen-free water to eliminate a non-volatile reagent in cases where the chemically-reduced dyestuff has low water solubility.

In particular distinction to prior art, addition of other chemical compounds which attract water such as $MgCl_2.6H_2O$, silica gel, glycerine, etc., have a negative effect on the rate of color return. Cellulose carriers such as 1–5% wt/vol hydroxyethyl cellulose or methyl-cellulose or similar thickening agents helpful in indicator deposition or printing are compatible with rapid color return.

In the practice of packaging, the reducing indicator dye should be in a highly visible location within the package or bottle (for example, in the neck or cap of the bottle). These locations would be highly accessible to air when the package is opened. To increase the shelf-life of the indicator by reducing trace-leakage or air into the package, the package could be sealed with a positive pressure of inert gas, e.g., nitrogen.

This invention is an improvement over the prior art where a package could be opened and later resealed without air (perhaps using freon from an aerosol can or $CO_2$ from a cartridge), and the indicator system, still containing reductant, would revert to its original color. Moreover, other previous security packaging of items or consumables in a readily-escaping acidic or alkaline gas together with a pH sensitive dye could compromise the contents of the package via chemical reaction. Therefore, the stable indicator of this invention which irreversibly turns a visible color in air and which furthermore can be used in packaging employing an inert atmosphere such as $N_2$ is a useful tool in packaging. Such an indicator can be utilized in oxygen-free packaging of perishable commodities and in tamper-resistant packaging application.

SPECIFIC EXAMPLES OF THE INVENTION

Example 1

Figure 1:
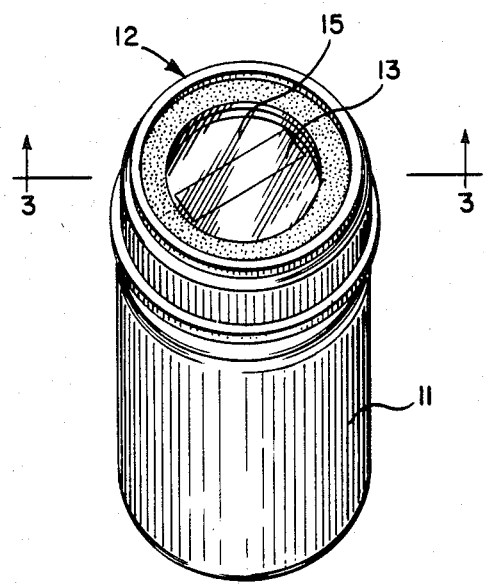
FIG. 1 is a sealed container of tablets with a transparent cap made in accordance with this invention.

An aqueous solution of methylene blue was formed having a concentration of 10 millimolar (mM). 45 microliters (μl) of the dye solution was reduced in the presence of nitrogen gas to the leuco state with 2.5 μl of triethylamine as the volatile alkaline agent and 2.5 μl 2-mercaptoethanol as the reducing agent. 10 μl of the reduced dye was spotted under nitrogen on Whatman #1 filter paper and dried in vacuum. Upon re-exposure to air, blue color returned very rapidly. The recovery of spectrophotometric absorbance at 665 nm following reduction and reoxidation was greater than 95% for methylene blue indicating little irreversible chemical bleaching. The threshold reduction conditions were 5 μl of 1:20 dilution of triethylamine and 2.5 μl of a 1:10 dilution of 2-mercaptoethanol in water.

Example 2

Example 1 was repeated using 5 μl triethylamine as the volatile alkaline agent and 5 μl ethanethiol as the reducing agent with similar results. The threshold reduction conditions were 2 μl of 100% triethylamine and 5 μl of 100% ethanethiol.

Example 3

Examples 1 and 2 were repeated using new methylene blue in place of methylene blue. Upon re-exposure to air the blue color returned almost immediately, more quickly than methylene blue, in both cases.

Example 4

Example 1 was repeated using thionine in place of methylene blue. The color reappeared more slowly than with methylene blue.

Example 5

Example 1 was repeated using 5 μl of ammonium hydroxide (58% solution) as the volatile alkaline agent.

Example 6

Example 5 was repeated using 5 μl of ethanethiol as the reducing agent.

Example 7

Examples 5 and 6 were repeated using new methylene blue in place of methylene blue.

In addition to the above examples, similar tests were made with methyl violet, with similar results. Also, other substrates tested successfully included glass, polypropylene, polyethylene, aluminum foil, glass fiber filter, DEAE filters, nitrocellulose filters, silica gel, dialysis membranes, and a variety of paper products.

The placement of the indicator in a container should establish unambiguously whether or not the container has been opened at any time after sealing by the manufacturer. The indicator is preferably visible from the outside of the container so that the status of the package can be checked at any time. Upon opening the container, the indicator changes color irreversibly. The indicator may be applied to virtually any inert surface or support as described above, as either a solution or liquid suspension with an optional carrier material, e.g., 1-5% wt/vol methylcellulose or hydroxyethylcellulose. This permits formation of the colored area in any desired shape or design, thereby adding specificity and improved protection. The leuco dye may be applied as a colorless spot, printed for example as the word "OPENED," or printed in the form of a company's logo to make counterfeiting difficult. At least one of the dyes (e.g., methylene blue) is nontoxic and is already utilized in the pharmaceutical industry, and has been approved by the Food and Drug Administration for internal consumption.

The indicator of this invention may be used with either solid packaged objects, e.g., pills, capsules, powders, or with packaged liquids, e.g., cough medicines, elixirs, etc. As shown in FIG. 1, the container 11 is sealed with an airtight closure 12. The indicator spot word or logo 13 is placed beneath the closure or cap 12 which is made of a transparent material so that the indicator can be viewed from the top. The contents 14 of the container 11 may be separated from the inside of this closure or cap by a thin membrane 15 adhering to the container rim and sealing the container but easily separable from it. This membrane permits the use of the indicator with liquid materials and is optionally used with dry materials affording the consumer added confidence in the integrity of the package. The membrane should be inert and impermeable to the contents of the container whether such contents be solid or liquid, but may be oxygen permeable or impermeable depending upon the requirements and goals of the packaging. Oxygen permeability protects against invasion of the package at any point other than the cap. The act of removing the cap or closure will initiate development of color in the indicator. The indicator can be mounted or printed directly on top of the membrane or inside the cap on an intermediate surface, e.g., a paper label which is, in turn, affixed to the above membrane or simply placed on top of the membrane. In some applications, especially with liquids, mounting the indicator directly on the membrane will assure the consumer's removal of the indicator from further involvement with the container and its contents. Direct printing or attachment of the indicator onto the sealing membrane creates a more tamper-resistant closure, since substitution or exchange of indicator elements between packages would be even more difficult. Substitution in any case would require air-free handling.

The descriptive label on the bottle or container should state the change to be expected in the indicator color upon opening the container. Furthermore, it should state that if this change does not occur, the contents should not be used and the item should be returned to the supplier. This insures against replacement of the original cap by an inert or substitute cap which is similar in appearance to the original.

Figure 2:
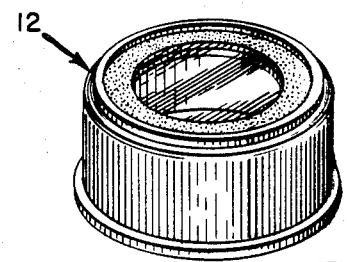
FIG. 2 is the container of FIG. 1 wherein the cap has been removed.
Figure 3:
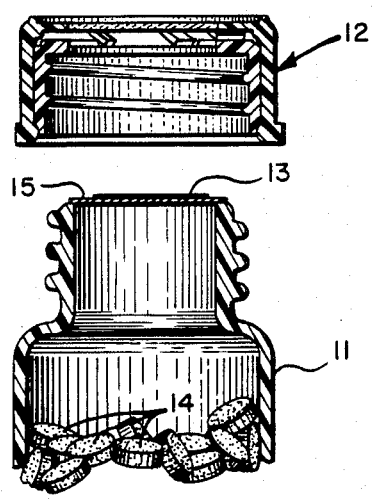
FIG. 3 is a section along 3—3 of FIG. 1.

As shown in FIG. 2, when the cap 12 is removed, the air displaces the nitrogen and the indicia dye 13 is oxidized and becomes colored. Resealing even with nitrogen will not change this color.

What is claimed is:

1. An oxygen indicator for use in an atmosphere free of oxygen, said indicator comprising a substrate carrying, in leuco state, a dye free of reducing agents and this reducing agent free dye being capable of irreversibly reacting with oxygen; said dye being characterized as being of the class which is reactive with oxygen to change from the leuco state to the colored state and which is reactive with reducing agent to change from the colored state to the leuco state.

2. The indicator of claim 1 wherein the dye is a basic thiazine dye.

3. The indicator of claim 1 wherein the dye is a triphenylmethane dye.

4. The indicator of claim 1 wherein the dye is methylene blue.

5. The indicator of claim 1 wherein the dye is new methylene blue.

6. The indicator of claim 1 wherein the dye is thionine.

7. The indicator of claim 1 wherein the dye is methyl violet.

8. The sealed package containing the indicator of claim 2 in an atmosphere free of oxygen.

9. A sealed package containing the indicator of claim 3 in an atmosphere free of oxygen.

10. A sealed package containing the indicator of claim 4 in an atmosphere free of oxygen.

11. A sealed package containing the indicator of claim 5 in an atmopshere free of oxygen.

12. A sealed package containing the indicator of claim 6 in an atmosphere free of oxygen.

13. A sealed package containing the indicator of claim 7 in an atmosphere free of oxygen.

14. A sealed package containing an oxygen indicator in an atmosphere free of oxygen, said indicator comprising a substrate carrying, in leuco state, a dye free of reducing agent and this reducing agent free dye being capable of irreversibly reacting with oxygen; said dye being characterized as being of the class which is reactive with oxygen to change from the leuco state to the colored state and which is reactive with reducing agent to change from the colored state to the leuco state.

15. The package of claim 14 wherein the atmosphere in nitrogen.

16. The package of claim 14 wherein the atmosphere is carbon dioxide.

17. The package of claim 14 wherein the atmosphere is argon.

18. The package of claim 14 wherein the atmosphere is a vacuum.

19. The package of claim 14 wherein the indicator is visible through a transparent portion of the package.

20. The package of claim 14 wherein the substrate is a membrane sealing the contents of the package, with the leuco dye being imprinted on the membrane, the dye being visible through a transparent portion in the package.

21. A sealed package containing an oxygen indicator to show whether tampering has occurred, comprising:
a hermetically-sealed container having a cap portion and a body portion,
said cap portion possessing a window in its top, and being capable of forming a hermetic seal with said body portion when said cap and body portions are joined together;
said cap and body being joined together to form said sealed container;
said container having therein an atmosphere free of oxygen;
a dye in leuco state, carried on a substrate;
said dye being free of reducing agent and being of the class which is reactive with oxygen to change from the leuco state to the colored state and which is reactive with reducing agent to change from the colored state to the leuco state;
said dye-carrying substrate being disposed and retained in said body so that it is visible through the window in said cap when cap and body are joined together and is capable of contacting surrounding air when the cap portion is removed;
whereby if the integrity of the package is broken, permitting oxygen from the air to contact said dye, the dye changes to its colored form irreversibly, to provide a warning.

* * * * *